United States Patent
Chuang et al.

(10) Patent No.: US 9,201,035 B2
(45) Date of Patent: Dec. 1, 2015

(54) GAS DETECTING SYSTEM, DEVICE AND METHOD

(75) Inventors: Chun-Te Chuang, Hsinchu (TW); Chun-Hsun Chu, Hsinchu (TW); I-Cherng Chen, Hsinchu (TW); Nai-Hao Kuo, Hsinchu (TW)

(73) Assignee: INDUSTRIAL TECHNOLOGY RESEARCH INSTITUTE, Hinchu (TW)

( * ) Notice: Subject to any disclaimer, the term of this patent is extended or adjusted under 35 U.S.C. 154(b) by 844 days.

(21) Appl. No.: 13/452,675

(22) Filed: Apr. 20, 2012

(65) Prior Publication Data
US 2013/0211732 A1 Aug. 15, 2013

(30) Foreign Application Priority Data
Feb. 9, 2012 (TW) .............. 101104165 A

(51) Int. Cl.
*G01N 27/12* (2006.01)
*G01N 33/00* (2006.01)

(52) U.S. Cl.
CPC .............. *G01N 27/12* (2013.01); *G01N 33/004* (2013.01); *G01N 33/0016* (2013.01); *G01N 33/0047* (2013.01); *G01N 33/0059* (2013.01)

(58) Field of Classification Search
CPC ....... G01N 27/12; G01N 27/02; G01N 27/04; G01N 27/122–27/124; G01N 27/14; G01N 27/16; G01N 27/18; G01N 33/0047; G01N 33/004; G01N 33/0016
See application file for complete search history.

(56) References Cited

U.S. PATENT DOCUMENTS

| | | | | |
|---|---|---|---|---|
| 4,580,439 | A | * | 4/1986 | Manaka ................. 73/31.06 |
| 4,627,269 | A | | 12/1986 | Forster |
| 5,517,182 | A | | 5/1996 | Yasunaga |
| 5,573,005 | A | * | 11/1996 | Ueda et al. ............. 600/543 |
| 6,128,945 | A | | 10/2000 | Shioiri |
| 6,705,152 | B2 | | 3/2004 | Routkevitch et al. |
| 6,739,180 | B2 | | 5/2004 | Huang |
| 6,767,732 | B2 | | 7/2004 | Alocilja |

(Continued)

FOREIGN PATENT DOCUMENTS

| CN | 2243080 Y | 12/1996 |
|---|---|---|
| CN | 1141433 | 1/1997 |

(Continued)

OTHER PUBLICATIONS

Pontes et al., "Classification of distilled alcoholic beverages and verification of adulteration by near infrared spectrometry," Food Research International, 39, 2006, pp. 182-189.

(Continued)

*Primary Examiner* — Manuel L Barbee
(74) *Attorney, Agent, or Firm* — Muncy, Geissler, Olds & Lowe, P.C.

(57) ABSTRACT

A gas detecting system, device and method use a variable pulse voltage waveform to increase the temperature of a detecting unit of the gas detecting system so it reacts with gas molecules from a particular space, and outputs a sensing signal. A processing unit of the gas detecting system then performs calculations on the sensing signal, such that an analysis unit may determine the presence of a target gas in the particular space, and further the composition and concentration of the target gas within the particular space, thus providing a detection that is accurate, rapid and convenient.

23 Claims, 7 Drawing Sheets

(56) References Cited

U.S. PATENT DOCUMENTS

| | | | |
|---|---|---|---|
| 6,844,197 | B1 | 1/2005 | Doleman |
| 6,960,476 | B2 | 11/2005 | Morris |
| 7,257,986 | B2 | 8/2007 | Haupt |
| 7,350,396 | B2 * | 4/2008 | Huang et al. .................. 73/23.2 |
| 7,460,958 | B2 * | 12/2008 | Walsh et al. ....... G01N 33/0034 702/24 |
| 7,680,607 | B1 | 3/2010 | Smulko |
| 2004/0113802 | A1 * | 6/2004 | Green et al. .................. 340/632 |
| 2007/0279633 | A1 * | 12/2007 | Yi et al. ........................ 356/432 |
| 2009/0120808 | A1 | 5/2009 | Wu |

FOREIGN PATENT DOCUMENTS

| | | |
|---|---|---|
| CN | 2401895 Y | 10/2000 |
| CN | 1478201 A | 2/2004 |
| CN | 1685223 | 10/2005 |
| CN | 101073007 | 11/2007 |
| CN | 101187647 | 5/2008 |
| CN | 101685078 | 3/2010 |
| CN | 201945551 U | 8/2011 |
| CN | 102243195 A | 11/2011 |
| EP | 0 698 786 A1 | 2/1996 |
| TW | 200419153 | 10/2004 |
| TW | M294034 | 7/2006 |
| TW | 200912297 | 3/2009 |
| TW | 200948967 A | 12/2009 |
| TW | 201105946 | 2/2011 |
| TW | 201115140 | 5/2011 |
| TW | 201126144 | 8/2011 |
| WO | WO 2008138661 | 11/2008 |

OTHER PUBLICATIONS

Yao et al., "Gas Sensor Array Based on Surface Acoustic Wave Devices for Vapors Detection and Analysis," Proceedings of the 2010 $5^{th}$ IEEE International Conference on Nano/Micro Engineered and Molecular Systems, Jan. 20-23, 2010, Xiamen China, pp. 267-271.

da Costa et al., "A novel strategy to verification of adulteration in alcoholic beverages based on Schlieren effect measurements and chemometric techniques," Microchemical Journal, 78, May 10, 2004. pp. 27-33.

Gutierrez-Osuna, "Pattern Analysis for Machine Olfation: A Review," IEEE Sensors Journal, Apr. 29, 2002, pp. 1-14.

Bermak et al., "Pattern Recognition Techniques for Odor Discrimination in Gas Sensor Array," Encyclopedia of Sensors, Edited by C.A. Grimes et al., vol. X, 2006, pp. 1-17.

Vergara et al., "Quantitative gas mixture analysis using temperature-modulated micro-hotplate gas sensors: Selection and validation of the optimal modulating frequencies," Sensors and Actuators B, 123, 2007, pp. 1002-1016.

Maziarz et al., "Gas sensors in a dynamic operation mode," Meas. Sci. Technol., 19, 2008, pp. 1-7.

Far et al., "A Bio-Inspired Pattern Recognition System for Tin—Oxide Gas Sensor Applications," IEEE Sensors Journal, vol. 9, No. 6, Jun. 2009, pp. 713-722.

Gosangi et al., "Active Tempterature Programming for Metal-Oxide Chemoresistors," IEEE Sensors Journal, vol. 10, No. 6, Jun. 2010, pp. 1075-1082.

Islam et al., "Porous Silicon based Organic Vapor Sensor Array for e-Nose Applications," IEEE Sensors, 2006, EXCO, Daegu Korea, Oct. 22-25, 2006, pp. 1085-1088.

Penza et al., "Recognition of Organic Solvents Molecules by Simultaneous Detection Using SAW Oscillator Sensors and Optical Fiber Devices Coated by Langmuir-Blodgett Cadmium Arachidate Films," IEEE Transactions on Ultrasonics, Ferroelectrics, and Frequency Control, vol. 53, No. 8, Aug. 2006, pp. 1493-1502.

* cited by examiner

GAS DETECTING SYSTEM, DEVICE AND METHOD

BACKGROUND

1. Technical Field

The present disclosure relates to active detecting techniques, and, more particularly, to a detecting system, a detecting device and a detecting method that can be easily operated to actively detect the presence of a target gas in a particular space.

2. Description of Related Art

Current gas detecting techniques based on metal oxide semiconductor technology offer the advantages of low cost, rapid measurement and long service life, and have been widely applied in the fields of home and industrial security. More specifically, the techniques generally use a sensor equipped with a metal oxide film and a heater to detect gas molecules, wherein the heater increases the temperature of the metal oxide film, such that the metal oxide film in the heating process reacts with the gas molecules in the environment, thereby changing the resistance of the metal oxide film to output a corresponding sensing signal. The sensing signal is then compared and analyzed to determine the various characteristics of the gas.

However, in actual use, the reaction between the metal oxide film and the gas molecules is limited by numerous environmental factors, such as temperature, humidity and the like, such that the output sensing signal is accompanied by a phenomenon called signal drift. As a result, accurate results in subsequent comparison and analysis may not be obtained. In addition, when the gas molecules are combined of gases in the same group, for example, methanol and ethanol, are mixed together, the reaction temperature and other characteristics of the gas molecules in the same group are very similar, so the current detection methods, upon completing comparison and analysis on the sensing signal, may have difficulties in obtaining accurate concentrations or mixing ratio of the gas molecules.

Existing detection methods can be found in prior-art publications, such as U.S. Pat. Nos. 6,739,180, 7,350,396, 7,460,958 and 7,680,607. U.S. Pat. Nos. 6,739,180 and 7,350,396 simply achieve detection through signal comparison, but they did not offer a solution to the problem of signal drift, and they lack sufficient accuracy in terms of concentration determination. In addition, they did not disclose any method for identifying the mixtures containing the gases in the same group, such as a mixture containing both methanol and ethanol. U.S. Pat. No. 7,460,958 determines concentrations according to a prediction module, but in its actual implementation, the method requires each sensor in a sensor array to perform self-diagnosis and compensation, and thus increasing the cost and time for detection. The chemical analyte technique proposed by U.S. Pat. No. 7,680,607 also requires a plurality of metal oxide sensors for signal comparison, thus resulting in waste of detection time and cost. In addition, it also fails to address the signal drift caused by the ambient temperature and humidity.

In another aspect, the implementations of the existing gas detecting technology usually require bulky and costly testing equipment. As such, it fails to analyze the gases in real time, and also hardly to be applied in our daily life. For example, the market is flooded with many poor-quality alcoholic beverages that contain harmful methanol, if one wishes to determine whether a beverage contains harmful substances, the only way is to retrieve samples of the alcoholic beverage and send them to specific authorities for time-consuming detection.

Therefore, there is a need for a solution that addresses the abovementioned and other shortcoming in the conventional gas detecting technique.

SUMMARY

In light of the foregoing drawbacks, an objective of the present disclosure is to eliminate the effects of the environmental factors and provide an active gas detecting technique that is user friendly.

In accordance with the above and other objectives, the present embodiments provides a gas detecting system, comprising: a database for storing at least one characteristic signal of at least one target gas; a voltage unit for outputting a variable pulse voltage waveform corresponding to the at least one target gas; a detecting unit for increasing its own temperature based on the variable pulse voltage waveform outputted by the voltage unit to react with gas molecules from a particular space, and to output a sensing signal corresponding to the gas molecules; a processing unit for performing a dimensionless or normalization calculation on the sensing signal outputted by the detecting unit according to a reaction temperature of the at least one target gas and outputting a relative signal; and an analysis unit for comparing a portion of the relative signal outputted by the processing unit with the at least one characteristic signal in the database to output an analysis result.

Furthermore, the present embodiments further provides a gas detecting device, comprising: a particular-space sampling system, a warning device and the above gas detecting system, wherein the particular-space sampling system retrieves gas molecules from a particular space for the gas detecting system to detect, and the warning device is used to receive the analysis result outputted by the gas detecting system and send out a corresponding warning message.

Moreover, the present embodiments also provides a gas detecting method, comprising: outputting a variable pulse voltage waveform corresponding to a target gas to a detecting unit; carrying out a temperature increasing procedure, by the detecting unit, upon receiving the variable pulse voltage waveform; reacting with gas molecules from a particular space, by the detecting unit while carrying out the temperature increasing procedure, to output a sensing signal corresponding to the gas molecules; performing a dimensionless or normalization calculation on the sensing signal according to a reaction temperature of the target gas and outputting a relative signal; and comparing a portion of the relative signal with a characteristic signals of the target gas in the database to output an analysis result.

In addition, the present embodiments further provides a gas detecting device, comprising: a housing with an opening; a particular-space sampling system connected to the opening of the housing; a gas detecting system provided within the housing for detecting a gas and outputting an analysis result; and a warning device provided within the housing for receiving the analysis result and sending out a warning message when the analysis result is larger than a predetermined value, wherein the gas detecting device conveys the gas to be detected to the housing via the particular-space sampling system.

BRIEF DESCRIPTION OF THE DRAWINGS

The present disclosure can be more fully understood by reading the following detailed description of the preferred embodiments, with reference made to the accompanying drawings, wherein.

DETAILED DESCRIPTION OF THE EMBODIMENTS

The present disclosure is described by the following specific embodiments. Those with ordinary skills in the arts can readily understand the other advantages and functions of the present disclosure after reading the specification. The present disclosure can also be implemented with different embodiments. Various details described in this specification can be modified based on different viewpoints and applications without departing from the scope of the present disclosure.

Figure 1:
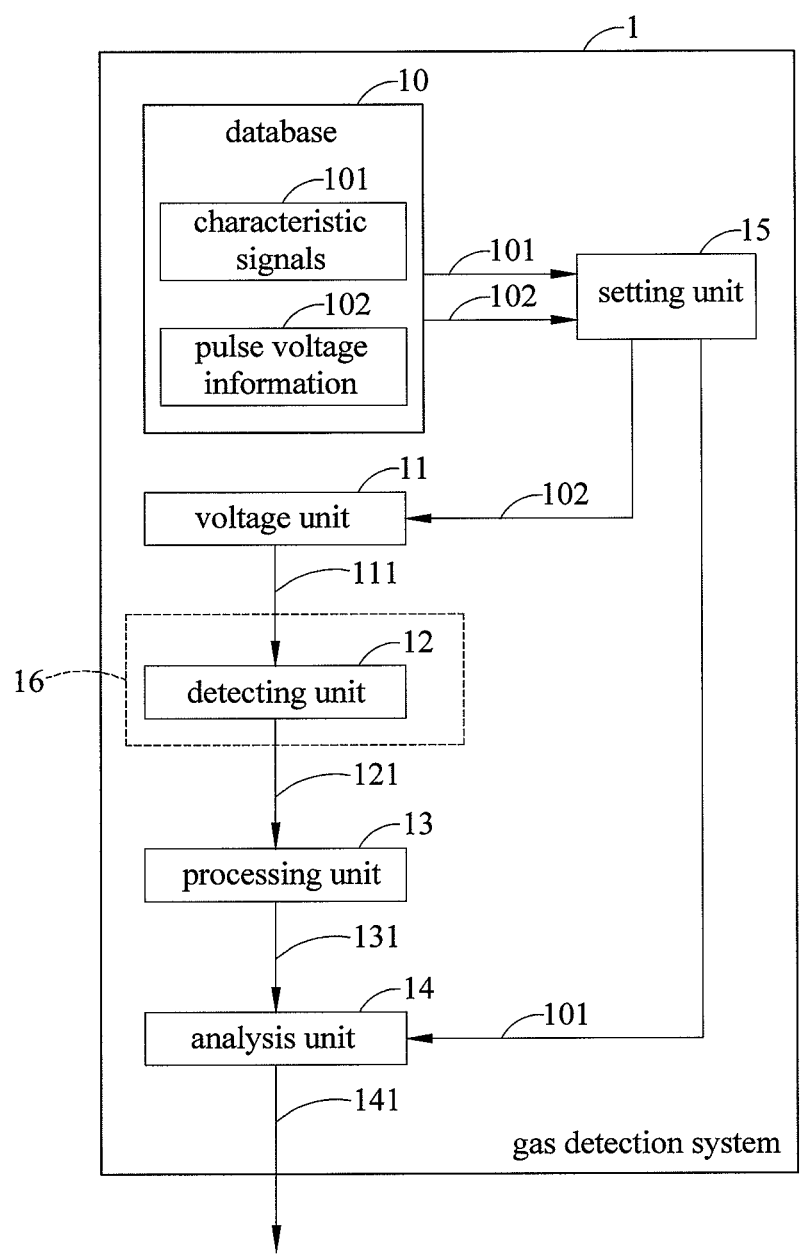
FIG. 1 is a block diagram showing a gas detecting system according to an embodiment of the present disclosure.
Figure 2:
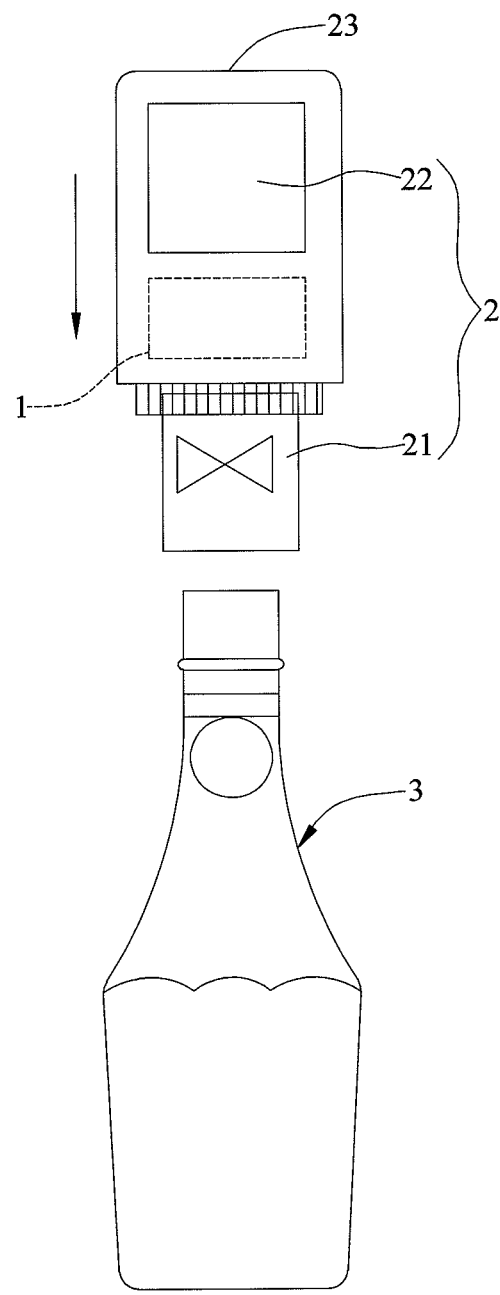
FIG. 2 is a schematic diagram illustrating application of the gas detecting device according to the present disclosure.
Figure 3:
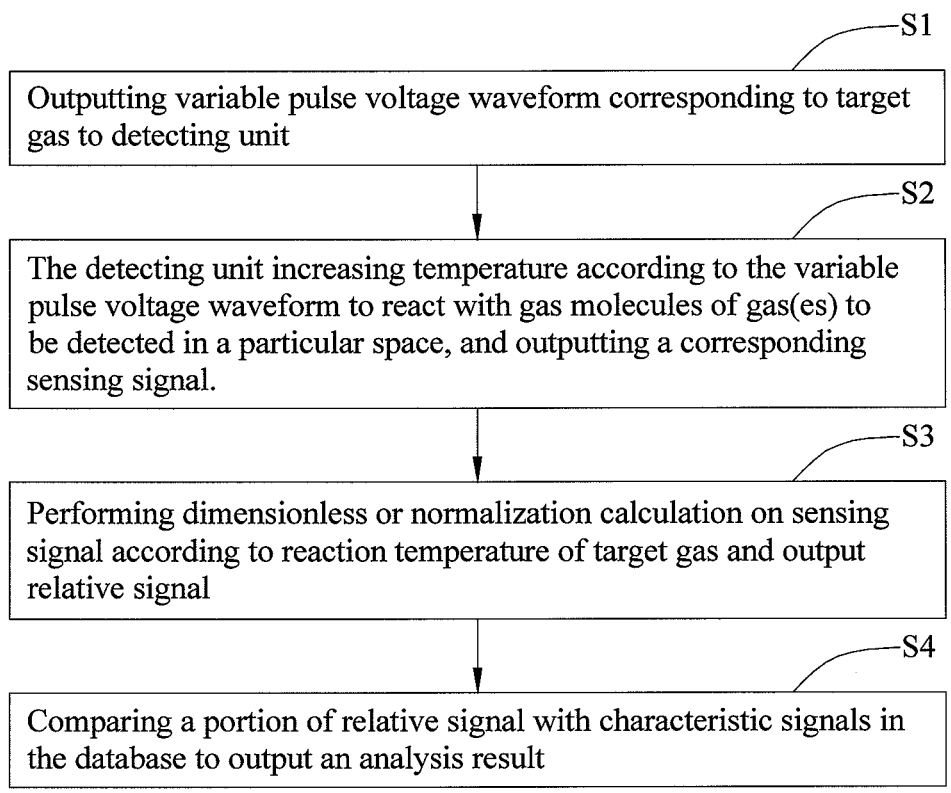
FIG. 3 is a flowchart illustrating a gas detecting method according to an embodiment of the present disclosure.
Figure 4:
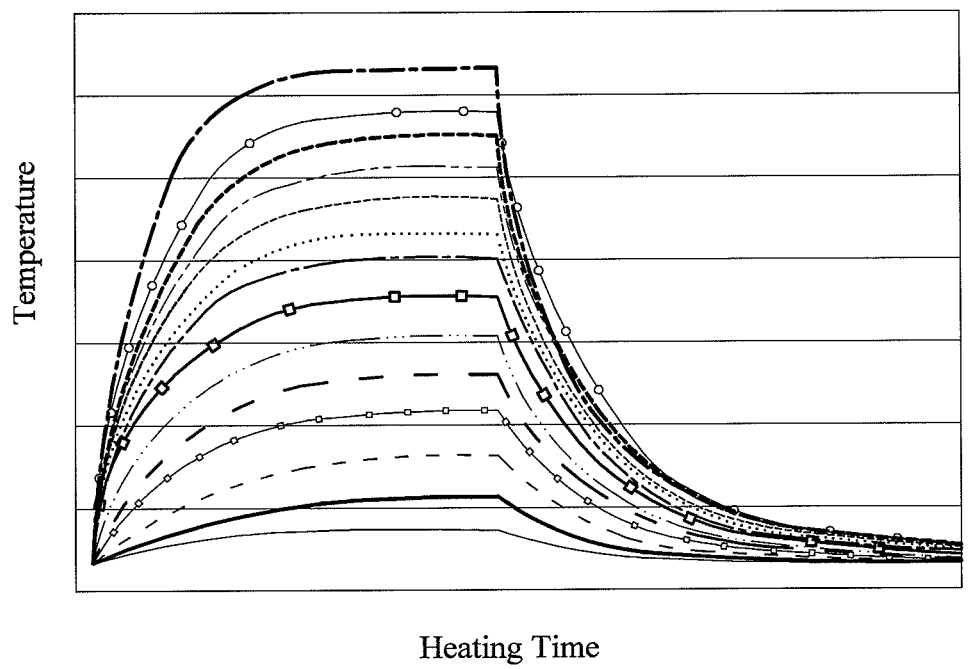
FIG. 4 is a graph depicting heating time versus reachable temperature of a detecting unit.
Figure 5:
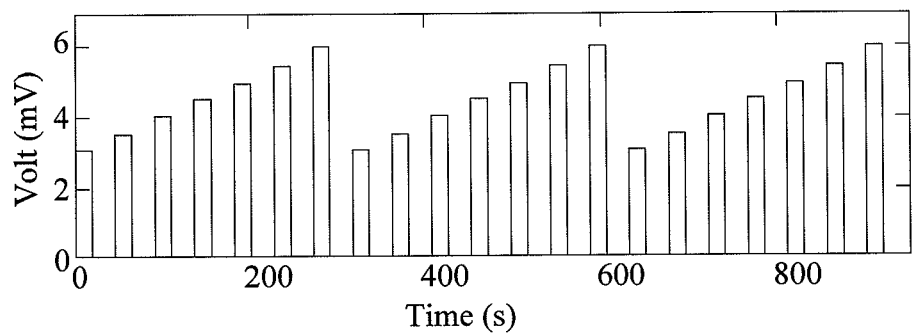
FIG. 5 is a graph depicting variable pulse voltage waveform according to an embodiment of the present disclosure.
Figure 6:
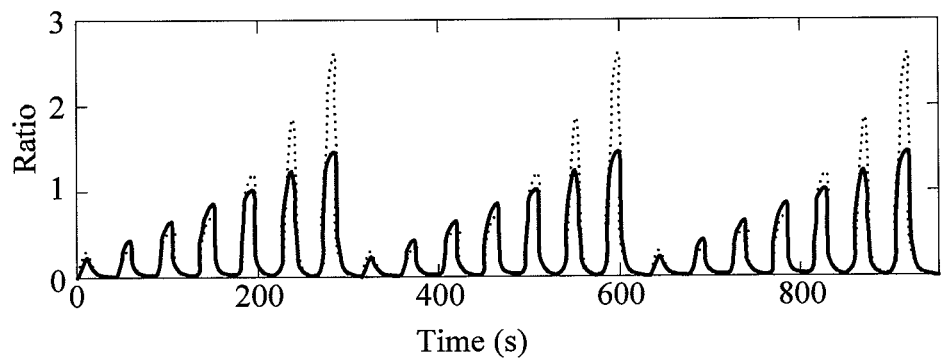
FIG. 6 is a graph depicting sensing signals of gas mixtures with different concentrations under the influences of ambient temperature and humidity.
Figure 7:
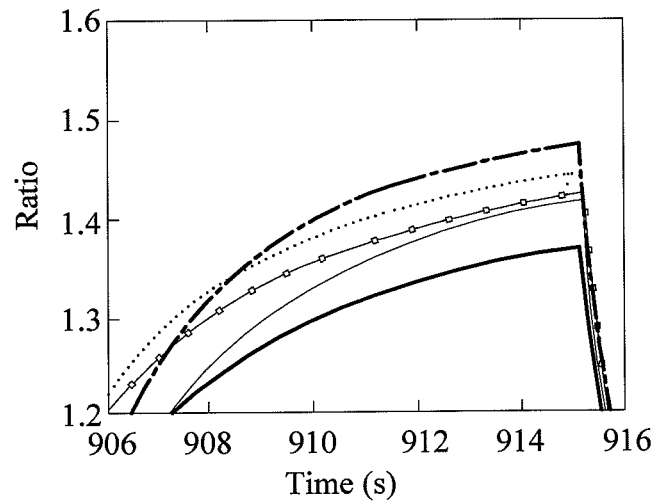
FIG. 7 is a graph of an enlarged portion of FIG. 6.
Figure 8:
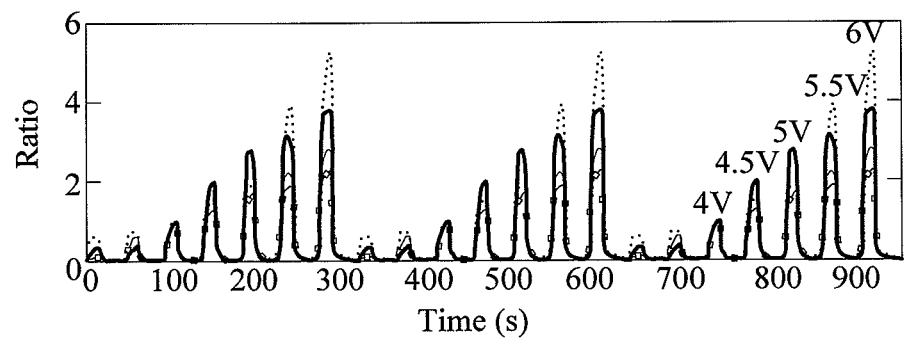
FIG. 8 is a graph showing relative signals of FIG. 6 after the environmental factors are removed.
Figure 9:
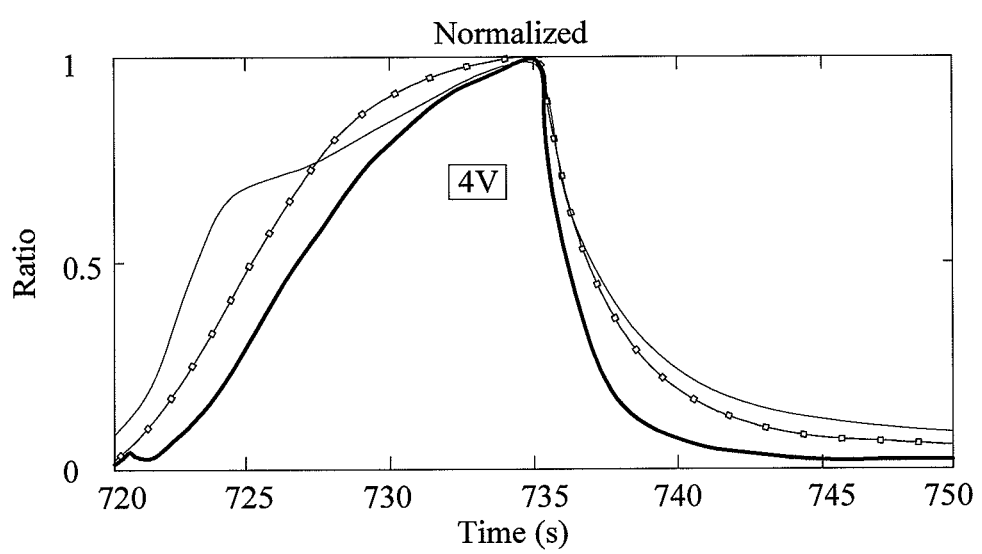
FIG. 9 is a portion of the relative signals shown in FIG. 8.
Figure 10:
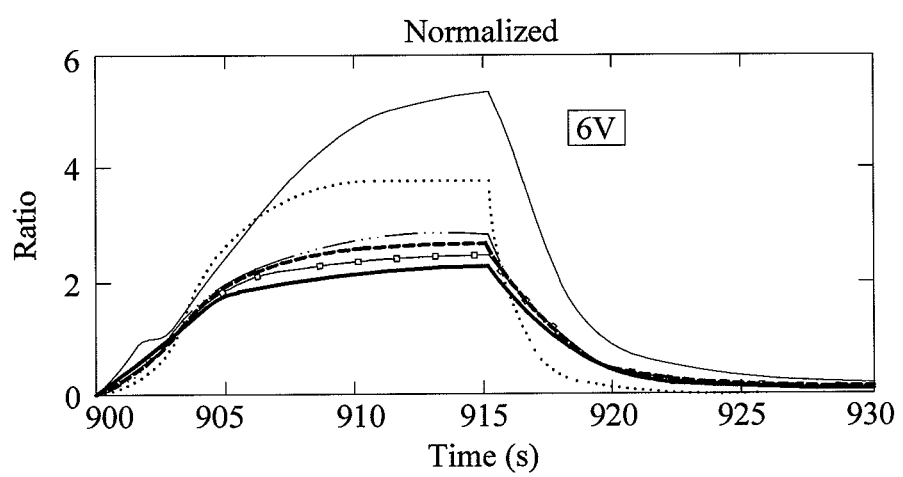
FIG. 10 is another portion of the relative signals shown in FIG. 8.
Figure 11:
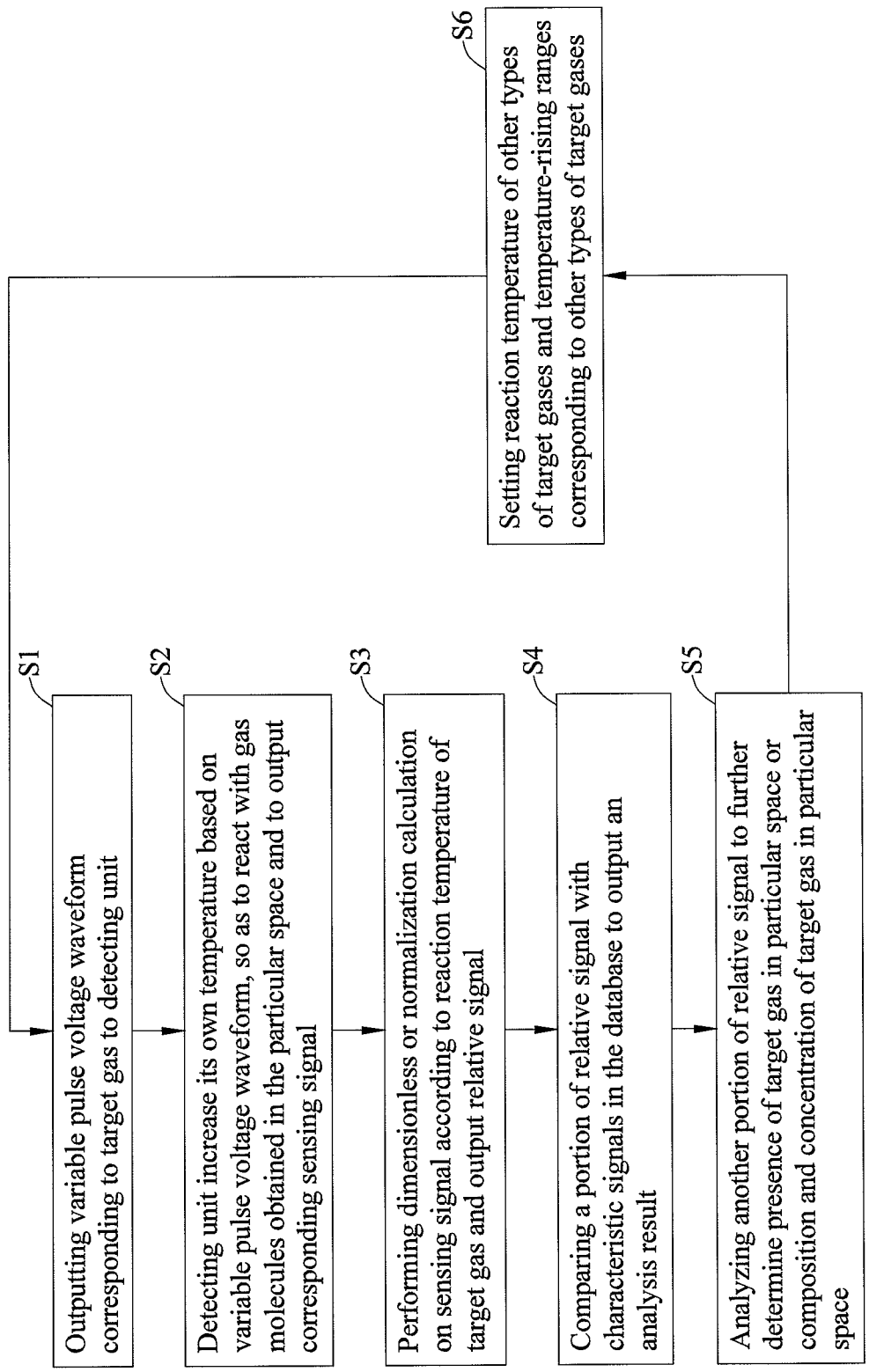
FIG. 11 is a flowchart illustrating a gas detecting method according to another embodiment of the present disclosure.

In order to understand a gas detecting system 1 and a gas detecting device 2 proposed by the present disclosure, descriptions are given below with respect to FIGS. 1 to 10, wherein FIG. 1 is a block diagram showing a gas detecting system according to an embodiment of the present disclosure, FIG. 2 is a schematic diagram illustrating application of the gas detecting device according to the present disclosure, FIG. 3 is a flowchart illustrating a gas detecting method according to an embodiment of the present disclosure, FIG. 4 is a graph depicting heating time versus reachable temperature of a detecting unit, FIG. 5 is a graph depicting variable pulse voltage waveform according to an embodiment of the present disclosure, FIG. 6 is a graph depicting sensing signals of gas mixtures with different concentrations under the influences of ambient temperature and humidity, FIG. 7 is a graph of an enlarged portion of FIG. 6, FIG. 8 is a graph showing relative signals of FIG. 6 after the environmental factors are removed, FIG. 9 is a portion of the relative signals shown in FIG. 8, FIG. 10 is another portion of the relative signals shown in FIG. 8, and FIG. 11 is a flowchart illustrating a gas detecting method according to another embodiment of the present disclosure.

As shown in FIG. 1, the gas detecting system 1 includes a database 10, a voltage unit 11, a detecting unit 12, a processing unit 13, an analysis unit 14 and a setting unit 15. The database 10 stores characteristic signals 101 and pulse voltage information 102 for at least one gas. The characteristic signals 101 include the reaction temperature and temperature-rising range of the gas. The pulse voltage information 102 is used to adjust the operation of the voltage unit 11. After the pulse voltage information 102 is transmitted to the voltage unit 11, the voltage unit 11 outputs a variable pulse voltage waveform 111 according to the pulse voltage information 102 to the detecting unit 12. Upon receiving the variable pulse voltage waveform 111, the detecting unit 12 performs corresponding temperature increase. In the meantime, the detecting unit 12 will react with the gas(es) to be detected 16 and accordingly output a sensing signal 121 to the processing unit 13. Upon receiving the sensing signal 121, the processing unit 13 performs preliminary processes to generate a relative signal 131. Then, the relative signal 131 is transmitted to the analysis unit 14, which compares the received relative signal 131 with the characteristic signals 101 in the database to generate a corresponding analysis result 141 to be outputted.

In an embodiment, the setting unit 15 is optionally included in the gas detecting system 1. If the characteristic signals 101 stored in the database 10 are only for a single gas, the gas detecting system 1 can simply transmit the characteristic signals 101 and the pulse voltage information 102 from the database 10 to the analysis unit 14 and the voltage unit 11. If the characteristic signals 101 stored in the database 10 are for more than one type of gas, the setting unit 15 may set the target gas, and the characteristic signals 101 and the pulse voltage information 102 for that target gas are transmitted. For example, when a user wishes to detect methanol, the target gas may be set as methanol, and the characteristic signals 101 and the pulse voltage information 102 corresponding to methanol are retrieved from the database 10 for use in the subsequent detection processes. The target gas may be methanol, ethanol, oxygen, carbon dioxide, or any other gases; the present disclosure is not limited to these.

FIG. 2 is a schematic diagram illustrating application of the gas detecting device according to the present disclosure. The gas detecting device 2 includes the gas detecting system 1, a particular-space sampling system 21, a warning device 22, and a housing 23, wherein the housing 23 is provided with an opening. The warning device 22 is disposed on the surface of the housing 23. The particular-space sampling system 21 is coupled to the opening of the housing 23. The gas detecting system 1 is contained within the housing 23. The particular-space sampling system 21 allows the gas detecting device 2 to be installed on the opening of a container 3, for example, so that the gas(es) to be detected 16 in the container 3 can be transmitted to the housing 23 via the particular-space sampling system 21, and the gas(es) to be detected 16 in the container 3 is/are detected using the gas detecting system 1. The particular-space sampling system 21 is, for example, a gas valve with an arbitrary connecting port to be correspondingly coupled to containers 3 with different opening sizes. The warning device 22 is used to receive the analysis result 141 output by the gas detecting system 1. When the analysis result 141 is larger than a predetermined value, warning information is displayed by the warning device 22, which can be observed by users. In an embodiment, the gas detecting device 2 can be designed to be of a form that is easily portable by users. Of course, the gas detecting device 2 can also be designed to be of a form that is to be fixed at a corner in a particular space; the present disclosure is not limited to these.

In order to understand the gas detecting method of the present disclosure, refer to FIG. 3 in conjunction with the descriptions for the gas detecting system 1 and the gas detecting device 2.

In step S1, the voltage unit 11 outputs a variable pulse voltage waveform 111 corresponding to the target gas. Then, proceed to step S2. In an embodiment, the target gas can be methanol, ethanol, oxygen, carbon dioxide, or volatile organic compounds.

In step S2, the detecting unit 12 of the gas detecting system 1 increases temperature according to the variable pulse voltage waveform output by the voltage unit 11 to react with gas molecules of gas(es) to be detected 16 from a particular space, and outputs a corresponding sensing signal 121. Then, proceed to step S3.

In an embodiment, before performing step S1, the method may further include the step of setting unit 15 setting the reaction temperature of the target gas and the temperature-rising range corresponding to the reaction temperature of the target gas. In step S2, the voltage unit 11 outputs a variable pulse voltage waveform 111 based on the set temperature-rising range. Furthermore, step S2 may further include the detecting unit 12 rising to a plurality of temperatures with different rates of temperature increase based on the variable pulse voltage waveform 111, and wherein the plurality of temperatures include the reaction temperature of the target gas set by the setting unit 15. The detecting unit 12 can be made of a metal oxide semiconductor, which increases its own temperature in step S2 so as to react with the gas(es) to be detected 16, thereby changing its resistance and outputting a sensing signal 121.

In step S3, the gas detecting system 1 performs a dimensionless or normalization process on the sensing signal 121 according to the reaction temperature of the target gas to output a relative signal 131 not affected by environmental factors. More specifically, the processing unit 13 of the gas detecting system 1 performs a dimensionless or normalization process on the sensing signal 121 output by the detecting unit 12 of the gas detecting system 1, and outputs a relative signal 131 not affected by environmental factors. Then, proceed to step S4. In this embodiment, step S3 may further include the step of processing unit 13 outputting relative signals 131 corresponding to different rates of temperature increase.

In step S4, the analysis unit 14 of the gas detecting system 1 analyzes and compares the characteristic signals 101 stored in the database 10 with a portion of the relative signal 131 outputted. If the portion of the relative signal 131 matches a characteristic signal 101, it means that the target gas corresponding to the characteristic signal 101 is detected from the gas molecules. Meanwhile, the analysis unit 14 of the gas detecting system 1 will creates an analysis result 141 indicating that the target gas or a gas in the same group of the target gas has been detected in the particular space. More specifically, the analysis unit 14 of the gas detecting system 1 can perform analysis on a portion of the relative signal 131 outputted by the processing unit 13 with the characteristic signals 101 in the database 10. When the portion of the relative signal 131 matches a characteristic signal 101 stored in the database 10, a signal is outputted, and the warning device 22 of the gas detecting device 2 with built-in gas detecting system 1 issues a corresponding warning message to promptly notify a user. In addition, in step S3, the processing unit 13 of the gas detecting system 1 may output relative signals 131 corresponding to different rates of temperature increase.

Furthermore, upon completing step S4, the analysis unit 14 of the gas detecting system 1 may perform analysis on another portion of the relative signal 131 outputted by the processing unit 13 with the characteristic signals 101 in the database 10 to further determine the presence of the target gas or the composition and concentration of the target gas in the particular space. When the composition and concentration of the target gas are analyzed, the warning device 22 of the gas detecting device 2 may issue a corresponding warning message based on the analyzed composition and concentration.

In particular, when the gas detecting device 2 is actually used to detect, for example, the presence of a target gas such as methanol in the particular space of the container 3, the particular-space sampling system 21 can be first installed in front of the opening of the container 3, and the setting unit 15 of the gas detecting system 1 is then used to set the heating time and reachable temperature of the detecting unit 12, as shown in FIG. 4, the reaction temperature of the methanol can be set at the intersection where temperature reaches 235° C. after heating at 4V for 15 seconds.

Moreover, the waveform graph of above variable pulse voltage waveform 111 can be that shown in FIG. 5 for providing different temperature increase rates. The detecting unit 12 may rise to a plurality of temperatures at different rates based on the variable pulse voltage waveform 111 inputted by the voltage unit 11. The plurality of temperatures may include the reaction temperature of the target gas.

The processing unit 13 performs a dimensionless or normalization process on the sensing signal outputted by the detecting unit 12 according to the reaction temperature of the target gas to output a relative signal 131 not affected by environmental factors. For example, the sensing signal 121 for gas mixtures of different concentrations outputted by the detecting unit 12 can be one shown in FIG. 6. When a curved portion of FIG. 6 is enlarged as shown by FIG. 7, it can be seen that the order of concentrations is not correct due to the effect of the signal drift. Thus, in order to eliminate the effect of the signal drift, the sensing signal 121 shown in FIG. 6 undergoes the dimensionless or normalization process to remove the effect of environmental factors, thereby outputting a relative signal 131 not affected by environmental factors. The outputted relative signal 131 can be as shown in FIG. 8. It should be noted that in the case of a single detecting unit 12, the plurality of sensing signals 121 shown in FIG. 6 are obtained through several times of measurements, but under the influences of factors such as the ambient temperature and humidity, even if they are enlarged as shown in FIG. 7, concentration ratios cannot be identified from the amplitudes, thus requiring the dimensionless or normalization process.

In particular, when the corresponding signal indicating heating at 4V is enlarged and shown in FIG. 9, it can be seen that profiles of different gases are different. Similarly, when the corresponding signal indicating heating at 6V is enlarged and shown in FIG. 10, it can be seen that the signal shift shown in FIG. 7 is lessened. In other words, due to differences in time and ratio, the plurality of relative signals 131 that appear to be overlapping on a single curve can be clearly distinguished from FIG. 9 or 10. For simplicity of the illustrations, although not specifically shown, the number of curves depicted in FIGS. 6 to 10 when viewed in a close-up view should correspond to each other. In addition, a portion of the relative signal 131 containing a number of concentrations depicted in FIG. 9 can also be stored in the database 10 as a characteristic signal for determining the presence of the target gas in the next operation. Another portion of the relative signal 131 containing a number of concentrations depicted in FIG. 10 can also be stored in the database 10 as a characteristic signal for identifying the composition and concentrations of the gas mixture in the next operation.

Furthermore, the analysis unit 14 compares the characteristic signals 101 stored in the database 10 with a portion of the relative signal 131 outputted by the processing unit 13. When the portion of the relative signal 131 matches a characteristic signal 101, an analysis result 141 indicating that the target gas or a gas in the same group of the target gas has been detected in the particular space is outputted. As a result of this, when the warning device 22 receives the analysis result 141 indicating that the target gas or a gas in the same group of the target gas has been detected in the particular space, it may further output a corresponding warning message.

In addition, in an embodiment, the warning device 22 can be a monitor or an alarm that notifies the user with image or sound that, for example, the target gas is detected in the gas molecules retrieved from the particular space in the container 3. As an example, when the target gas is set to be methanol, and the warning device 22 issues a warning message, it can mean that methanol is contained in the gas molecules given out from the solution in the container 3, so the user seeing this message may promptly stop drinking it. Of course, the particular space can also be an indoor or outdoor local area.

In this embodiment, when the analysis unit 14 determines that a portion of the relative signal 131 matches a characteristic signal 101 stored in the database 10, another portion of the relative signal 131 outputted by the processing unit 13 can be further analyzed and compared with the characteristic signals 101 stored in the database 10. For example, another portion of the relative signal 131 corresponding to a different rate of temperature increase and voltage is analyzed to further determine the presence of the target gas in the particular space or the composition and concentration of the target gas in the particular space, wherein another portion of the relative signal 131 used as the basis of analysis and comparison can be one shown in FIG. 10. In an embodiment, after the composition and concentration of the target gas are determined, the warning device 22 may further issue a corresponding warning message corresponding to the composition and concentration, for example, by using graphic or textual warning to notify the user the concentration of the methanol in the particular space.

It should further be noted that after the heating time and reachable temperature as those shown in FIG. 4 are set using the setting unit 15, a variable pulse voltage waveform 111 shown in FIG. 5 can also be set. The temperature of the detecting unit 12 of the gas detecting system 1 is increased based on the variable pulse voltage waveform 111, so as to react with the gas molecules of the gas(es) to be detected 16 retrieved by the particular-space sampling system 21. Also, it can be seen from FIG. 5, each pulse lasts for 15 seconds and pauses for 30 seconds. The pulse voltage starts from 3V and rises to 6V with an increment of 0.5V each time.

Furthermore, after the variable pulse voltage waveform 111 is inputted, the detecting unit 12 of the gas detecting system 1 will start to operate and react with the gas molecules and output one of the sensing signals 121 shown in FIG. 6. Meanwhile, the sensing signals 121 are affected by signal shift, so the whole set of sensing signals 121 is divided by the signal value of heating at 4V for 15 seconds, normalizing them into corresponding signals, thereby removing the effect of signal shift. In an embodiment, the corresponding signal 131 may form one of the waveforms shown in FIG. 8.

After the normalization or dimensionless process, the analysis unit 14 of the gas detecting system 1 may first analyze a portion, such as the relative signal corresponding to a 4V pulse waveform, and compare the characteristics of this portion of the corresponding signal 131 with the characteristic signals 101 stored in the database 10 to determine whether the particular space of the container 3 includes the target gas. If the presence of the target gas or a gas in the same group of the target gas is detected, the warning device 22 further outputs a corresponding warning message to notify the user.

Next, if the particular space is found to possibly have the presence of the target gas, the analysis unit 14 of the gas detecting system 1 may further compare another portion of the corresponding signal 131 corresponding to a 6V pulse waveform shown in FIG. 10 to determine the composition and concentration of the target gas in the particular space.

It should be noted that the gas detecting system 1 of the present disclosure or the gas detecting device 2 including the gas detecting system 1 of the present disclosure, apart from detecting a single type of gas in the particular space for the user, it may further detect other types of gases in the particular space. For example, after methanol detection is completed, the detection for other types of gases such as ethanol, liquefied petroleum gas, methane, or hydrogen sulfide can be made. For example, after detection for a first target gas (e.g. methanol) is completed, detection for a second target gas (e.g. liquefied petroleum gas) can automatically be carried out, in which the variable pulse voltage waveform 111 can be set based on the characteristics of liquefied petroleum gas, and a sensing signal 121 corresponding to liquefied petroleum gas is outputted, which is converted into a relative signal 131 corresponding to liquefied petroleum gas, and a portion of the relative signal 131 is analyzed again to determine the presence of liquefied petroleum gas in the particular space. Similarly, if analysis indicates the liquefied petroleum gas or a second target gas in the same group of liquefied petroleum may possibly exist, another portion of the relative signal 131 corresponding to liquefied petroleum gas is analyzed to determine the composition and concentration of liquefied petroleum gas in the particular space. This type of detection is also suitable for the detection of a plurality of target gases.

In other words, after another portion of the relative signal 131 is analyzed to determine the possible composition and concentration of a type of target gas in the particular space, the setting unit 15 may further re-establish the reaction temperature and corresponding temperature-rising range of another type or other types of target gas(es). The gas detecting system 1 repeats the implementing steps as mentioned above, and through similarly analysis, the possible composition and concentration of the another type or other types target gas(es) in the particular space can be outputted. The detailed implementing steps can be as shown in FIG. 11.

In addition, the gas detecting device 2 is designed to correspond to the implementation of the container 3. The particular-space sampling system 21 may be designed to be removably attached to the opening of the container 3 via a screw or a snap. In an embodiment, the housing of the gas detecting device 2 may also be provided with associated activating switch for turning on the gas detecting system 1 built in the gas detecting device 2. In other embodiments, the gas detecting device 2 may also be designed to be like a clock with built-in gas detecting system 1, and can be secured to a particular space of an office, for example, in order to detect oxygen, carbon dioxide, volatile organic compounds emitted by printers or the like. Moreover, the particular-space sampling system 21 of the gas detecting device 2 can also be designed variable-volume sampling structure. After retrieving the gas molecules of the gas(es) to be detected 16 in the particular space of the container 3, this structure can vary its volume in order to increase the content in unit volume of the gas molecules, thereby increasing the accuracy of the subsequent detection.

It should also be noted that particular space may include a target gas, gases in the same group of the target gas, or gases in the different groups of the target gas. Accordingly, based on the principle of operations described before, in the case that the particular space only contains one type of target gas (e.g. pure ethanol), only a portion of the relative signal is needed to determine the presence of the target gas, and another portion of the relative signal is used to determine its concentration. In the case that the particular space contains a target gas and a gas in the same group of the target gas (e.g. 1% ethanol+99% methanol), if one portion of the relative signal has detected the target gas or the gas in the same group of the target gas, then another portion of the relative signal will determine the presence of the target gas and its composition and concentration. In the case that the particular space contains a target gas and a gas in the different group of the target gas, sine the reaction temperatures of the target gas and the gas in the different group of the target gas are different, the sensing signal obtained will be similar to a combination of the two. Thus, a portion of the relative signal may determine the possible presence of the target gas or the gas in the same group of the target gas, and another portion of the relative signal will determine the presence of the target gas and its composition and concentration. In the case that the particular space contains a gas in the same group of the target gas and a gas in the different group of the target gas, sine the reaction temperatures of the gas in the same group of the target gas and the gas in the different group of the target gas are different, the sensing signal obtained will be similar to a combination of the two. Thus, a portion of the relative signal may determine the possible presence of the target gas or the gas in the same group of the target gas, and another portion of the relative signal will determine the presence of the target gas and its composition and concentration.

In summary, the gas detecting technique of the present disclosure uses a variable pulse voltage waveform to increase temperature for reacting with the gas molecules, and further performs the dimensionless or normalization process to eliminate the influence of environmental factors, thereby accurately determining whether a particular space includes a target gas as well as its composition and concentration. As such, the present disclosure provides a method that promptly and accurately detects a target gas in a particular space, meeting the needs of all sectors.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A gas detecting system, comprising:
   a database for storing at least one characteristic signal of at least one target gas;
   a voltage unit for outputting a variable pulse voltage waveform corresponding to the at least one target gas;
   a detecting unit for increasing its own temperature based on the variable pulse voltage waveform outputted by the voltage unit to react with gas molecules from a particular space, and to output a sensing signal corresponding to the gas molecules;
   a processing unit for performing a dimensionless or normalization calculation on the sensing signal outputted by the detecting unit according to a reaction temperature of the at least one target gas and outputting a relative signal; and
   an analysis unit for comparing a portion of the relative signal outputted by the processing unit with the at least one characteristic signal in the database to output an analysis result.

2. The gas detecting system of claim 1, further comprising a setting unit for selecting one of the at least one characteristic signal stored in the database in order to set the reaction temperature of the at least one target gas and a temperature-rising range corresponding to the reaction temperature of the at least one target gas.

3. The gas detecting system of claim 2, wherein the detecting unit increases to a plurality of temperature at different rates based on the variable pulse voltage waveform, and the plurality of temperature include the reaction temperature of the at least one target gas.

4. The gas detecting system of claim 3, wherein the relative signals outputted by the processing unit correspond to the different rates.

5. The gas detecting system of claim 1, wherein the detecting unit increases its own temperature based on the variable pulse voltage waveform to react with the gas molecules to change its own resistance, and outputs the sensing signal.

6. The gas detecting system of claim 1, wherein when the analysis unit determines that the portion of the relative signal matches one of the at least one characteristic signal, it further compares another portion of the relative signal outputted by the processing unit with the one of the at least one characteristic signal in the database to determine the at least one target gas in the particular space presence or a composition and a concentration of the at least one target gas in the particular space.

7. A gas detecting device, comprising:
   a particular-space sampling system for retrieving gas molecules from a particular space;
   a gas detecting system for detecting the gas molecules retrieved by the particular-space sampling system, including:
   a database for storing at least one characteristic signal of at least one target gas;
   a voltage unit for outputting a variable pulse voltage waveform corresponding to the at least one target gas;
   a detecting unit for increasing its own temperature based on the variable pulse voltage waveform outputted by the voltage unit to react with the gas molecules retrieved by the particular-space sampling system, and to output a sensing signal corresponding to the gas molecules;
   a processing unit for performing a dimensionless or normalization calculation on the sensing signal outputted by the detecting unit according to a reaction temperature of the at least one target gas and outputting a relative signal; and
   an analysis unit for comparing a portion of the relative signal outputted by the processing unit with the at least one characteristic signal in the database to output an analysis result; and
   a warning device for receiving the analysis result outputted by the analysis unit and accordingly sending out a warning message.

8. The gas detecting device of claim 7, wherein the particular-space sampling system includes a variable-volume sampling structure that changes volume upon retrieving the gas molecules of the particular space to increase the content per unit volume of the gas molecules.

9. The gas detecting device of claim 7, wherein the gas detecting system further comprises a setting unit for selecting one of the at least one characteristic signal stored in the database in order to set the reaction temperature of the at least one target gas and a temperature-rising range corresponding to the reaction temperature of the at least one target gas.

10. The gas detecting device of claim 9, wherein the detecting unit increases to a plurality of temperature at different rates based on the variable pulse voltage waveform, and the plurality of temperature include the reaction temperature of the at least one target gas.

11. The gas detecting device of claim 10, wherein the relative signals outputted by the processing unit correspond to the different rates.

12. The gas detecting device of claim 7, wherein the detecting unit increases its own temperature based on the variable pulse voltage waveform to react with the gas molecules retrieved by the particular-space sampling system to change its own resistance, and outputs the sensing signal.

13. The gas detecting device of claim 7, wherein when the analysis unit determines that the portion of the relative signal matches one of the at least one characteristic signal, it further compares another portion of the relative signal outputted by the processing unit with the one of the at least one characteristic signal in the database to determine one of the at least one target gas in the particular space presence or a composition and a concentration of the one of the at least one target gas in the particular space.

14. A gas detecting method, comprising steps of:
outputting a variable pulse voltage waveform corresponding to a target gas to a detecting unit;
carrying out a temperature increasing procedure, by the detecting unit, upon receiving the variable pulse voltage waveform;
reacting with gas molecules from a particular space, by the detecting unit while carrying out the temperature increasing procedure, to output a sensing signal corresponding to the gas molecules;
performing a dimensionless or normalization calculation on the sensing signal according to a reaction temperature of the target gas and outputting a relative signal; and
comparing a portion of the relative signal with a characteristic signal of the target gas in the database to output an analysis result.

15. The gas detecting method of claim 14, wherein the variable pulse voltage waveform is based on the reaction temperature of the target gas and a temperature-rising range corresponding to the reaction temperature of the target gas.

16. The gas detecting method of claim 15, wherein the temperature increasing procedure raising the detecting unit to a plurality of temperature at different rates based on the variable pulse voltage waveform, and the plurality of temperature include the reaction temperature of the target gas.

17. The gas detecting method of claim 16, wherein the relative signal correspond to the different rates.

18. The gas detecting method of claim 14, wherein, in the temperature increasing procedure, the detecting unit reacts with the gas molecules to change its own resistance, and outputs the sensing signal.

19. The gas detecting method of claim 14, further comprising comparing another portion of the relative signal with the characteristic signal of the target gas to determine the target gas in the particular space presence or a composition and a concentration of the target gas in the particular space.

20. The gas detecting method of claim 14, further comprising repeating the steps for determining another target gas in the particular space presence or another composition and another concentration of the another target gas.

21. A gas detecting device, comprising:
a housing with an opening;
a particular-space sampling system connected to the opening of the housing; and
a gas detecting system provided within the housing for detecting a gas, wherein the gas detecting system includes a database, a detecting unit, a processing unit and an analysis unit, the processing unit performs a dimensionless or normalization calculation on a sensing signal outputted by the detecting unit according to a reaction temperature of the gas and outputs a relative signal, the analysis unit compares a portion of the relative signal outputted by the processing unit with at least one characteristic signal in the database to output an analysis result; and
a warning device provided within the housing for receiving the analysis result and sending out a warning message when the analysis result is larger than a predetermined value,
wherein the gas detecting device conveys the gas to be detected to the housing via the particular-space sampling system.

22. The gas detecting device of claim 21, wherein the particular-space sampling system is a valve having a connection port with an arbitrary size for correspondingly connecting with containers with variable sizes for detecting the gas in the containers.

23. The gas detecting device of claim 21, wherein the gas to be detected include at least one of methanol, ethanol, oxygen and carbon dioxide.

* * * * *